(12) United States Patent
Koma et al.

(10) Patent No.: US 7,517,678 B2
(45) Date of Patent: Apr. 14, 2009

(54) METHOD FOR PROTEIN PRODUCTION

(75) Inventors: Daisuke Koma, Chiba (JP); Kuniki Kino, Tokyo (JP); Toshiya Sawai, Chiba (JP)

(73) Assignees: Waseda University, Tokyo (JP); Chisso Corporation, Osaka (JP)

( * ) Notice: Subject to any disclaimer, the term of this patent is extended or adjusted under 35 U.S.C. 154(b) by 0 days.

(21) Appl. No.: 11/366,285

(22) Filed: Mar. 2, 2006

(65) Prior Publication Data

US 2006/0199249 A1    Sep. 7, 2006

(30) Foreign Application Priority Data

Mar. 2, 2005    (JP)    .............................. 2005-058193

(51) Int. Cl.
| | |
|---|---|
| *C12P 1/00* | (2006.01) |
| *C12P 21/06* | (2006.01) |
| *C12P 21/04* | (2006.01) |
| *C12N 9/00* | (2006.01) |
| *C12N 9/10* | (2006.01) |
| *C12N 9/48* | (2006.01) |

(52) U.S. Cl. ..................... 435/193; 435/69.1; 435/70.1; 435/71.1; 435/183; 435/41; 435/212

(58) Field of Classification Search ........................ None
See application file for complete search history.

(56) References Cited

FOREIGN PATENT DOCUMENTS

| | | | |
|---|---|---|---|
| JP | 2669859 B2 | 5/1989 | |
| JP | 6-30772 A | 2/1994 | |
| JP | 2004-24243 A | 1/2004 | |
| WO | WO 02/29030 A2 * | 4/2002 | |

OTHER PUBLICATIONS

Ngo et al., in The Protein Folding Problem and Tertiary Structure Prediction, 1994, Merz et al. (ed.), Birkhauser, Boston, MA, pp. 433 and 492-495, Ref: U, Form-892.*
Kashefi et al., Science, 2003, 301: p. 934.*
Life below the limit, [online], Retrieved from the Internet on Oct. 30, 2006, <http://www.astrobio.net/news/modules.php?op=modload&name=News&file=article&sid=2120&mode=thread&order=0&thold=0>.*
Luthi et al., Applied and Environmental Microbiolgy, Sep. 1990, p. 2677-2683.*
Potrykus, Gene transfer to cereals: an assessment, Biotechnology, 1990, 8(6):535-542.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Kovarova et al. (Temperature-dependent growth kinetics of *E. coli* ML30 in glucose-limited continuous culture, Journal of Bacteriology, 1996, pp. 4530-4539).*

* cited by examiner

*Primary Examiner*—Rebecca E Prouty
*Assistant Examiner*—Jae W Lee
(74) *Attorney, Agent, or Firm*—Leydig, Voit & Mayer, Ltd.

(57) ABSTRACT

Provided is a novel comprising culturing host cells into which a foreign gene has been introduced for producing a protein in a soluble form encoded by the foreign gene, recombinant cells are cultured in the temperature range lower than or equal to the upper temperature limit for growth of the host cells and higher than 5 degrees below the upper temperature limit for growth of the host cells after induction of expression.

5 Claims, 8 Drawing Sheets

SEQUENCE LISTING

<160> NUMBER OF SEQ ID NOS: 14

<210> SEQ ID NO 1
<211> LENGTH: 1230
<212> TYPE: DNA

<213> ORGANISM: Aeropyrum pernix

<400> SEQUENCE: 1

| | | | | | |
|---|---|---|---|---|---|
| gtgaactggc | tgttgcccca | gaaggatcct | accctggaca | tccaggagag | ggttgttgag | 60 |
| atagagggtg | agactgcttt | cgcatacctc | gcagtggcca | ggaagctgat | ccaggagggt | 120 |
| aggcgcgtaa | taagctttgg | gataggccag | cccgacttcc | cgacgcccca | tcacattaga | 180 |
| gaggctgcga | agaaggcttt | agacgagggg | ttcacaggct | ataccgagac | ggccgggata | 240 |
| ccggagctga | gggaggctat | cgcatggtac | ctcaactcca | ggtacggggc | cgacgtgtct | 300 |
| ccggaggagg | ttatagccac | gacggggct | aagactgcaa | tattcctggg | tatggccctc | 360 |
| tacctgaggc | cgggagacga | ggtcataata | ccggacccca | gctactacgc | ctacgcacag | 420 |
| gtggctaaac | tcttcggcgc | caggcccgtt | tacgttccaa | tgaagtttga | gccgggtcta | 480 |
| gggttcaggt | tcgatatcga | ggggatagaa | agggctgtga | gcgagaagac | gaggatgata | 540 |
| gttgtcaaca | accccacaa | ccccacgggg | agtgttttcc | cgccggacca | ggtggaggcg | 600 |
| atacacgata | tagcgaggag | gaggggccta | ataatactgg | ccgacgagat | atacgacaac | 660 |
| ttcctctaca | cggagaagcc | cttcaagagc | accctctccc | tcccagactg | gagggagaac | 720 |
| ctcgtttacg | tcaacggttt | cagcaagaca | ttcagcatga | cgggctggag | gctcggctat | 780 |
| gttgtgctca | ggagggaggt | aatcccgaag | gccctagacc | tcgcagtcac | aatatacagc | 840 |
| tgccccccca | gcatagctca | gaaggctggc | gtcgccgcgc | tcagaggcga | ctgggtcct | 900 |
| gtgagagaga | tggtagaaga | gttcaggagc | agagcgagga | tactttacga | catactatcc | 960 |
| caggccgagg | gtatagagcc | ctacctcccg | gagggcgcct | tctacatgtt | ccccgtgtg | 1020 |
| gccggcctcc | tgaggaagac | ggggctcagc | gtggagcagc | tcgcggagaa | gctgctatac | 1080 |
| agctacggcg | tcctggtcct | gcccggcacc | agcttccctg | agagtgttgg | cagggagcat | 1140 |
| gttaggctga | gcttcgccac | ggccaccagc | gacgtgaagg | aggggcgga | gataatagtc | 1200 |
| agggcgtcta | gggagctgtc | cagcggctag | | | | 1230 |

<210> SEQ ID NO 2
<211> LENGTH: 31
<212> TYPE: DNA
<213> ORGANISM: Artificial
<220> FEATURE:
<223> OTHER INFORMATION: primer1

<400> SEQUENCE: 2
cccaaaccat atgaactggc tgttgcccca g         31

<210> SEQ ID NO 3
<211> LENGTH: 30
<212> TYPE: DNA
<213> ORGANISM: Artificial
<220> FEATURE:
<223> OTHER INFORMATION: primer2

<400> SEQUENCE: 3
ccgaattcct agccgctgga cagctcccta          30

<210> SEQ ID NO 4
<211> LENGTH: 20
<212> TYPE: DNA
<213> ORGANISM: Artificial
<220> FEATURE:
<223> OTHER INFORMATION: primer3

<400> SEQUENCE: 4

-continued

```
taatacgact cactataggg                                         20

<210> SEQ ID NO 5
<211> LENGTH: 19
<212> TYPE: DNA
<213> ORGANISM: Artificial
<220> FEATURE:
<223> OTHER INFORMATION: primer4

<400> SEQUENCE: 5
gctagttatt gctcagcgg                                          19

<210> SEQ ID NO 6
<211> LENGTH: 1365
<212> TYPE: DNA
<213> ORGANISM: Pyrococcus horikoshii

<400> SEQUENCE: 6
atggagttga agccaaacgt taaagagata cccggaccaa agctaggaa agttattgag    60 gagcaccaca agtacatggc aaccacgaca acgatccaa acgagtactt cctagttatc   120
gagagggcag agggagttta ttggatcgat gtcgatggaa acgtactctt ggatttctcc   180
tcaggaatcg gtgtcatgaa cgtaggactt aggaatccaa aagttattga ggccataaag   240
aagcaacttg atctggtact tcacgctgct gggactgact actataaccc atatcaagta   300
gaacttgcaa agaagctcgt tgagatagcc ccaggagaca tcgaaagaaa ggtcttccta   360
agcaatagtg ggaccgaggc caatgaggca gcgttaaaga tagcaaagtg gtccacaaac   420
aggaagatgt tcatagcctt cattggagca ttccatggaa gaacccatgg aactatgagc   480
cttaccgcga gtaaacctgt ccagagaagc agaatgttcc caacgatgcc tggtgtagtt   540
catgttccat atccaaatcc atacagaaat ccatggggaa ttgatggtta tgaaaaccca   600
gatgagttga taaatagggt aatcgactac attgaagagt acctctttga gcactacgtt   660
ccagccgaag aagttgccgg aatattcttt gaacccatcc aaggtgaggg aggttacgta   720
gttccaccaa agaacttctt caaagagctc aagaaattgg cagataagca tggaatactc   780
ttaatagacg atgaagttca gatgggaatg ggaagaactg gaaggatgtg gccatagag   840 cacttcgata tcgttcccga tatagttacc gttgcaaagg cccttggtgg tggaataccc   900
atcggagcga ctatattcag agctgacctt gactttggag tcagcggtgt tcacagcaac   960
acattcggag gaaacactgt cgctgcagct gcagcccttg cggtgataga agagcttcag  1020
aatggtttaa tagagaatgc ccagaagctg gaacctctct tcagggagag gcttgaggag  1080
atgaaagaga gtatgagat aatcggtgat gtaagaggcc ttggacttgc atggggagtt  1140
gagttcgtta agataggaa gaccaaggaa tatgcaacca aggaaagagg agaaatagtt  1200
gtcgaagccc ttaagagagg tttagcattg cttggctgtg gaaagagtgc aataaggctt  1260
atcccaccat tgataatcag tgaagaagag gcaaagatgg gattggatat ctttgaggaa  1320
gcaataaagg tcgtcagcga aaggcacgga tacaagattc attag                 1365

<210> SEQ ID NO 7
<211> LENGTH: 35
<212> TYPE: DNA
<213> ORGANISM: Artificial
<220> FEATURE:
<223> OTHER INFORMATION: primer5

<400> SEQUENCE: 7
```

```
cccaaaccat atggagttga agccaaacgt taaag                                    35
```

<210> SEQ ID NO 8
<211> LENGTH: 31
<212> TYPE: DNA
<213> ORGANISM: Artificial
<220> FEATURE:
<223> OTHER INFORMATION: primer6

<400> SEQUENCE: 8

```
ccgaattcct aatgaatctt gtatccgtgc c                                        31
```

<210> SEQ ID NO 9
<211> LENGTH: 1359
<212> TYPE: DNA
<213> ORGANISM: Aeropyrum pernix

<400> SEQUENCE: 9

```
gtggctgttg atgcaccccg gatagttgtg gagcccccgg gccctagggc tagggaggtc         60
ctcgagaggg acgagagggt tataatgcag tctttcactc gctggtaccc cctggttgtt        120
aaacgtggct acggggctgt ggtggaggat gttgacggca acaggtatat agacttcaac        180
gctggtatag cagtgttgaa cgtgggccac aatcacccta gggttgttga ggcggttaaa        240
cgccagctgg agaggttcct gcactatagc ctgacggact tctactatga ggaggccgtc        300
tccgccgcgg agaggcttgc cagatccgtc cccataagcg gcggggccaa gacgttcttc        360
accaacagcg gggccgagag catcgaggcc tccataaagg ttgtaagggc gttcttcagg        420
gggacgaggc cctacataat aagcttcctc gggggcttcc acggaggac ctacggggcc         480
atgagcgcct cagccagcaa gccggtccac agggccaggt tctaccccct cgtcccgggc        540
ttcatccacg ccccatcccc agaccatac cgctgcccct tccccggcct cgagggtgaa         600
gcgtgtggcg aggcggctgt aagctatata gaggactata tattctcgaa gctggtcgac        660
ccgggagagg ttgccgcatt cctcttcgag cccatccagg gcgagggcgg ctacgtcgtc        720
ccgcccgaca gcttcctacc ctcgctccag aagctggcta ggaagcatgg gatactgctc        780
atcgcggacg aggttcagac gggcttcgcg aggacgggca ggatgttcgc cgtggagcac        840
tgggttgtgg agccagatgt catggcccta gccaaagcca tgggagggg gctgccgctg         900
ggggctgcgg tggggaggag cgaggtgatg agcctccccc gcggtagcca cgccaacact        960
ttcggcggca accccgtcgc cctcgccgcc ttcaacgcgg tgatggacgt tatagagggc       1020
gagaggctgt gggagaggtc gcagaggctg ggcgagaagg cgctgaagat actggggag        1080
gctgccgagg agctgagtat agtgggccat gtgaggggta aggggctaat gataggcgtt       1140
gagctggtca gggacgagaa caccaggag ccccacaagg aggccctcgc ctgggtgctg        1200
gataggtctt tcaagagggg tcttctagtg ataggcgcgg gcgtctcagc cgtgaggata       1260
gcgcccccgc tcaccatcga ggaggagctc ttcgaccggg gtctggagat actggtggag       1320
gtcctcaggg aggccgaccg ccgcttctcc caggtctag                              1359
```

<210> SEQ ID NO 10
<211> LENGTH: 30
<212> TYPE: DNA
<213> ORGANISM: Artificial
<220> FEATURE:
<223> OTHER INFORMATION: primer7

<400> SEQUENCE: 10

```
cccaaaccat atggctgttg atgcaccccg                                          30
```

<210> SEQ ID NO 11
<211> LENGTH: 28
<212> TYPE: DNA
<213> ORGANISM: Artificial
<220> FEATURE:
<223> OTHER INFORMATION: primer8

<400> SEQUENCE: 11
ccgaattcct agacctggga gaagcggc                                      28

<210> SEQ ID NO 12
<211> LENGTH: 1199
<212> TYPE: DNA
<213> ORGANISM: Sulfolobus tokoda i i

<400> SEQUENCE: 12
atgccagtag atgattttc cctttcggca aatagtatat caggagaatc taccctagta    60
tatcaagatg ttgcaagaca agtacagaag actaagggaa taagaatcat aaattttggt   120
ataggacaac cggatttgcc tacatttgcc agaataagag aagctgcaaa gaaatcattg    180
gatgaaggat ttactggcta tacatcagct tatggaattg atgaattaag acaaaagata    240
gcagagcatt taagcagtaa atatgagagt gtgagaaagg aagaagttat tgtaactcct    300
ggggcaaaaa cggcactta cttagccttt ttattataca taaatcctgg agacgaagtt     360
ataatatttg acccttcatt ttactcttat gcagaagtag taaagatgtt aggaggagtc    420
ccagtttatg ttaaaatgaa gtttaatgag agtactggat tttctcttaa cttatcggaa    480
ttagaatcta aaataaataa aaaaacaaaa atgatagtat taaataatcc tcataatcca    540
acaggtatgg tgtttgatcc aatagaaatt gaaaagctaa tggagattac taaggaaaag    600
aaagttcttc ttctatcaga tgaaatatat gattatttta tttatgaagg aaagatgaag    660
agtgtactag aagatccaga ttggagagac tatgttattt atgtaaatgg attcagtaaa    720
acgttctcta tgactggttg gaggttaggg tatgtagtag ctaaagaaaa agtgattaag    780
aaaatggcag agattgctgc aaatatttat acttgtccta ctagttttgc tcagaaaggt    840
gcattagcag cttttgaatc ttttgatgaa gttaaggaaa tgatatcatt atttaaaaag    900
agaagggata taatgtacga agaacttaag aaaataaaag gaatacaagt gcataaaagt    960
caaggagcgt tctacatgtt tccatttatt ggcgagattc taaaaaaggc taatcttagt   1020
gttaaagact tttcgttaaa gttaattgag gaaaaaggag taaccaccat accgggtgaa   1080
gtattcccat tagaagttgg taaagatttt gttaggctta gttttgctgt aaaagaagat   1140
gatataagag aaggtataaa aaggatgaaa gagtttattg atatgttgat gacacctga    1199

<210> SEQ ID NO 13
<211> LENGTH: 37
<212> TYPE: DNA
<213> ORGANISM: Artificial
<220> FEATURE:
<223> OTHER INFORMATION: primer9

<400> SEQUENCE: 13
cccaaaccat atgccagtag atgatttttc cctttcg                             37

<210> SEQ ID NO 14
<211> LENGTH: 35
<212> TYPE: DNA
<213> ORGANISM: Artificial
<220> FEATURE:

```
<223> OTHER INFORMATION: primer10

<400> SEQUENCE: 14
ccgaattctc aggtgtcatc aacatatcaa taaac                                35
```

METHOD FOR PROTEIN PRODUCTION

CROSS REFERENCE TO RELATED APPLICATIONS

This application claims the benefit of priority to Japanese Patent Application No. 2005-58193, filed on Mar. 2, 2005, which is incorporated herein by reference.

TECHNICAL FIELD

The present invention relates to methods for producing proteins.

DESCRIPTION OF THE RELATED ART

In protein production, gene recombination technology has developed, by which proteins can be produced in large amounts using recombinant cells made by introducing an expression vector containing a gene encoding a protein of interest into host cells. In particular, to produce a protein of interest in large amounts and easily recover the produced protein, expression systems in microorganisms such as *E. coli*, yeast, *bacillus subtilis*, actinomycetes, fungi, etc. have been used.

However, when a heterologous gene has been expressed in a expression system in microorganism, most or all of the expressed proteins has been accumulated as insoluble protein aggregates called inclusion bodies in many cases. Thus, a method by which such insoluble proteins can be isolated in an active and solubilized state has been desired.

For example, there is disclosed a method for activating insoluble hydantoinase produced in recombinant bacteria, in which, after insoluble hydantoinase that has been produced in recombinant bacteria and accumulated as insoluble aggregates was solubilized by adding 2-mercaptoethanol or urea, the solubilized hydantoinase is activated under the presence of Mn ions (Japanese Laid-Open Application No. 1994-30772).

Further, there is disclosed a protein-renaturing method, in which a cysteine-containing protein is solubilized, being converted into a reduced and denatured state by a denaturing agent and a reducing agent, its disulfide bonds are formed at the sites corresponding to those observed in the natural protein by removing the reducing agent and oxidizing the protein in a denaturing condition, and then the renatured protein is isolated and purified (Japanese Patent No. 2669859).

As described in the above, to obtain a protein of interest that has physiological activity from inactive insoluble protein aggregates folded into the form (tertiary structure) that does not give its intrinsic physiological activity, it was necessary to treat the aggregates with a denaturing solution containing a denaturing agent such as guanidine hydrochloride and urea and a reducing agents such as β-mercaptoethanol, cysteine, and glutathione, unfold polypeptides in the aggregates, and subsequently refold them into an active conformation.

Such a method for unfolding and refolding insoluble protein aggregates, not only requires enormous efforts in considering conditions but also involves complicated operations such as removal of the denaturing agent by dialysis, gel filtration, etc. In addition, renaturation efficiency is sometimes extremely low.

Meanwhile, there is disclosed a method for producing a protein by culturing host cells in which a introduced foreign gene can be inducibly expressed, in which a protein of interest can be obtained in an active state by inducing expression of the foreign gene in the low temperature range of 12° C. to 25° C., preferably 21 to 25° C. (Japanese Laid-Open Application No. 2004-24243).

SUMMARY OF THE INVENTION

The object of the present invention is to provide a novel method for obtaining a protein of interest efficiently in a soluble form when the protein is produced by expression of a foreign gene in host cells such as microorganisms etc.

The inventors found that an insoluble protein can be recovered efficiently in an active form in the production of transaminase proteins by culturing *E. coli* into which an expression vector containing a thermophile-derived transaminase gene has been introduced at 46° C. after inducing expression of the transaminase gene, and have thus accomplished the present invention based on these findings.

The present invention encompasses the following:

1. A method for, by culturing a host cell into which a foreign gene has been introduced, producing a protein encoded by the foreign gene, which includes culturing the host cell, after inducing expression of the foreign gene, in the temperature range lower than or equal to the upper temperature limit for growth of the host cell and higher than 5° C. below the upper temperature limit for growth of the host cell.
2. The production method of claim 1, wherein the host cell is *E. coli*.
3. A method for, by culturing a host cell into which a foreign gene has been introduced, producing a protein encoded by the foreign gene, which includes culturing the host cell, after inducing expression of the foreign gene, in the temperature range higher than 42° C. and equal to or lower than 47° C.
4. The production method of claim 1, wherein the foreign gene is derived from a thermophile.

It should be noted herein that thermophiles refer to microorganisms whose optimum growth temperature is 50° C. or higher, and which hardly thrive at 40° C. or lower. Among thermophiles, microorganism whose optimum growth temperature is 50 to 70° C. is referred to as moderate thermophiles, microorganism whose optimum growth temperature is 70° C. or higher is referred to as extreme thermophiles, and microorganisms whose optimum growth temperature is 80° C. or higher is referred to as hyperthermophiles. In addition, mesophiles refer to microorganisms whose growth temperature is in the normal temperature environment, especially those whose optimum growth temperature is 20 to 40° C. Psychrophiles refer to microorganism whose optimum growth temperature is 20° C. or less.

DESCRIPTION OF THE PREFERRED EMBODIMENT

Figure 1:
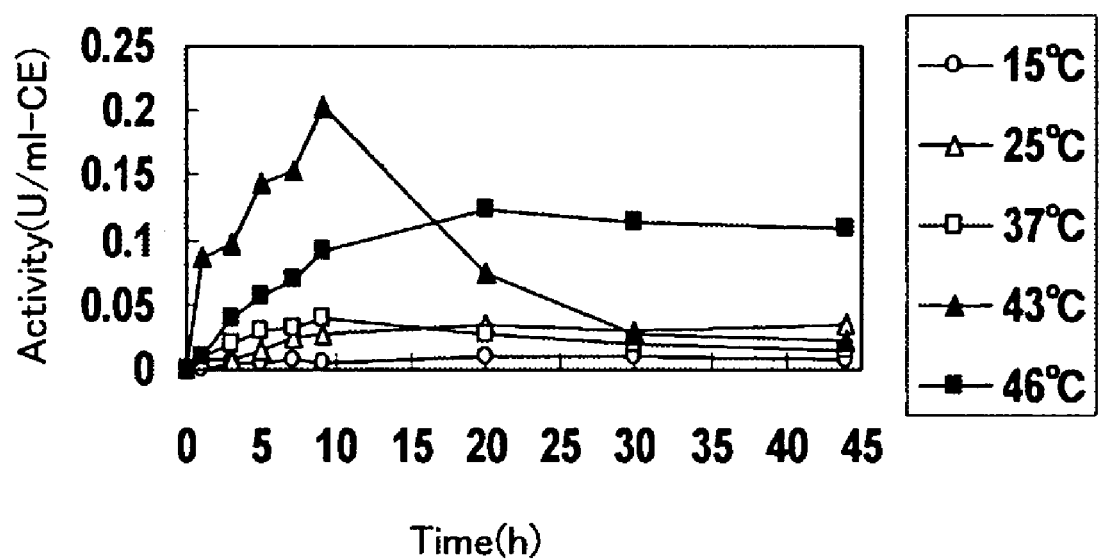
FIG. 1 shows a result of a measurement of enzyme activity in Example 1 performed according to the present invention.

Embodiments of the present invention accomplished based on the above-described findings are hereinafter described in detail by giving Examples. Unless otherwise explained, methods described in standard sets of protocols such as J. Sambrook and E. F. Fritsch & T. Maniatis (Ed.), "Molecular Cloning, a Laboratory Manual (3rd edition), Cold Spring HarborPress and Cold Spring Harbor, N.Y. (2001); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or alternatively, modified/changed methods from these are used. When using commercial reagent kits and measuring apparatus, unless otherwise explained, attached protocols to them are used.

The objective, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are for illustrative and explanatory purposes only and are not intended to restrict the invention to these embodiments or examples. It is further apparent to those skilled in the art that various changes and modifications may be made based on the descriptions given herein within the intent and scope of the present invention disclosed herein.

The present invention provides a method for producing a protein by culturing host cells into which a foreign gene has been introduced, in which the host cells are cultured after inducing expression of the foreign gene, in the temperature range lower than or equal to the upper temperature limit for growth of the host cells and higher than 5 degrees below the upper temperature limit for growth of the host cells.

In this method, the host cells are not particularly limited but can be appropriately selected from various eukaryotic and prokaryotic cells. In particular, it is preferred that host cells have the system in which the expression of a protein is regulated by at least one promoter whose activity can be induced with an inducer to express the gene. *E. coli*, bacteria of the genus *Bacillus*, and yeast are particularly preferred hosts, among which *E. coli* is the most preferred because of ease of culture, known genome information, well known characteristics of the strains, high expression levels of recombinant proteins, availability of various host-vector systems, etc.

The foreign genes and their encoding proteins include, but not limited to, for example, genes derived from thermophiles, such as hyperthermophiles, extreme thermophiles, and moderate thermophiles, etc; mesophiles; and psychrophiles. The present invention can be applied to any gene and protein.

In the method for producing a protein according to the present invention, the culture temperature after inducing expression is near the upper temperature limit for growth of a host. For this reason, when using a mesophile, such as *E. coli*, *B. subtilis*, yeast, etc. as a host, the foreign gene is derived preferably from a thermophile, such as a hyperthermophile, an extreme thermophile, and a moderate thermophile, etc; and a mesophile, and more preferably from a thermophile, such as a hyperthermophile, an extreme thermophile, and a moderate thermophiles, etc.

The expression vector into which a foreign gene encoding a protein of interest has been incorporated is not particularly limited and a known expression vector may be used. The expression vector include, for example, *E. coli*-derived plasmids, such as the pET derivatives, pBR derivatives, pUC derivatives, etc; *B. subtilis*-derived plasmids, such as the pUB110 derivatives, pC194 derivatives, etc; yeast-derived plasmids, such as pPIC6, pAUR123 DNA, etc; and vectors made by inserting various promoters for expression of foreign genes into animal virus vectors such as adenoviruses or insect virus vectors such as baculovirus.

These expression vectors may optionally contain a gene encoding a protein to be coexpressesed, such as a selective marker, chaperonin, etc. Examples of the selection marker include a chloramphenicol resistance gene, an ampicillin resistance gene, a tetracycline resistance gene, etc.

The method for incorporating a foreign gene into an expression vector is not particularly limited, and known methods may be used. One example of the method is to digest the aforementioned foreign gene with restriction enzymes and ligate it into an expression vector that has been digested with the same restriction enzymes. The most appropriate method can be selected depending on the type of foreign gene, expression vector etc. to be used.

The method for introducing an expression vector into a host cell is not limited, but can appropriately be selected depending on the type of host cell and vector etc. to be used. Examples of the method include electroporation, heat shock method, etc.

In the expression systems that have the above-described composition, a protein of interest is expressed, for example, in the following methods.

First, recombinant transformed with an expression vector harboring a foreign gene encoding the protein of interest are cultured. The medium for culturing recombinant cells is not particularly limited, and appropriately selected depending on the hosts to be used. In the method according to the present invention, it is necessary to induce expression in recombinant cells when they are cultured. The suitable timing for the induction is, when using *E. coli* as the host, for example, is the point when the cell concentration in the culture measured as the absorbance at 660 nm (OD660) is 0.05 to 3.0, preferably 0.50 to 1.0.

As the inducer, known agents may be used and it can be appropriately selected depending on the type of promoter and host cell, etc. For example, when the host is *E. coli*, 3-β-indole acrylic acid (IA) can be used for the trp promoter; and isopropyl β-thiogalactopyranoside (IPTG), etc. can be used for the lac promoter and tac promoter. When the host is yeast, methanol, etc. can be used for the AOX1 promoter and AUG promoter.

After the expression of the protein is induced in the recombinant cells, the cells are cultured in the temperature range lower than or equal to the upper temperature limit for growth of the host cells and higher than 5 degrees below the upper temperature limit for growth of the host cells; preferably in the temperature range lower than or equal to the upper temperature limit for growth of the host cells and higher than or equal to 3 degrees below the upper temperature limit for growth of the host cells; more preferably in the temperature range lower than or equal to the upper temperature limit for growth of the host cells and higher than or equal to 1 degree below the upper temperature limit for growth of the host cells. For example, when using *E. coli* Rosetta (DE3), of which upper temperature limit for growth is 47° C., recombinant cells are cultured in the temperature range higher than 42° C. to 47° C., preferably in the temperature range equal to or higher than 44° C. to 47° C., more preferably in the temperature range equal to or higher than 46° C. to 47° C. By growing the host cells under such conditions, a protein of interest can be efficiently obtained in an active form.

The protein that has been expressed can be isolated and purified by known methods. For example, after the cells are disrupted by sonication, with a homogenizer, or the like and the cell debris is removed by centrifugation or the like, the protein can be isolated and purified by ammonium sulfate precipitation, gel chromatography, ion exchange chromatography, affinity chromatography, etc. Alternatively, when a tag, such as a His tag, a GST tag, a Flag tag, etc. is fused to a protein, the protein can be isolated and purified by affinity chromatography using an appropriate column such as nickel column, depending on the tag. Alternatively, depending on the purpose, the conditioned medium or cell homogenate can be used.

Hereinafter, the present invention will be explained in more detail with reference to Examples. However, the present invention is by no means limited by these Examples.

EXAMPLE 1

1. Method for Preparing of Recombinant Cells into which a Foreign Gene Has Been Incorporated In this Example, the transaminase gene (APE2248) of the hyperthermophile *Aeropyrum pernix* was used as a foreign gene. The hyperthermophile *Aeropyrum pernix* is an aerobic hyperthermophile harvested by Kyoto University in 1993 in a hydrothermal vent at Kodakara Island in Kagoshima Prefecture. Its genome information has been published by the National Institute of Technology and Evaluation.

First, DNA that has the nucleotide sequence shown in SEQ ID NO: 1 was amplified from the genome of *Aeropyrum pernix* by a PCR reaction. As primers for the PCR reaction, DNAs shown in SEQ ID NOs: 2 and 3 were used. The PCR reaction was performed using KOD plus polymerase (manufactured by Toyobo Co., Ltd.), according to the protocol attached to this enzyme. After the reaction, 5 μg/μl DNA solution was obtained by purifying the amplified DNA fragments using GFX PCR and Gel Band Purification Kit (manufactured by Amercham), according to the protocol of the kit.

Next, the restriction enzymes EcoRI and NdeI (1 μl each), 5 μl of 10×H Buffer, (all of which are manufactured by Takara Bio Inc.) and 43 μl of the DNA solution obtained as above were mixed and incubated at 37° C. overnight.

Meanwhile, 2 μl of 0.5 μg/μl pET21a(+), (which is manufactured by Novagen) 1 μl of EcoRI, 1 μl of NdeI, and 5 μl of 10×H Buffer (which are manufactured by Takara Bio Inc.) were mixed and incubated at 37° C. overnight. The genomic DNA and plasmid digested with the restriction enzymes were purified by agarose electrophoresis. DNAs were recovered from the gel with GFX PCR and Gel Band Purification Kit (manufactured by Amersham) and ligated with DNA Ligation Kit Ver.2 (manufactured by Takara Bio Inc.) according to the protocol of the kit. Then, *E. coli* JM109 competent cells was transformed with the resulting recombinant plasmids by the electroporation method.

The transformed cells were spread onto LB agar plates (1.0% Tryptone, 0.5% Yeast Extract, 1.0% NaCl) containing 50 μg/ml ampicillin and incubated at 37° C. overnight. Clones that have the fragment of interest were identified by colony direct PCR from several colonies selected randomly from single colonies formed on the agar medium and then directly suspended in a reaction solution. Colony direct PCR was performed in a total volume of 50 μl of reaction mixture freshly prepared.

| | |
|---|---|
| Ex Taq polymerase (manufactured by Takara Bio Inc.) | 0.5 μl |
| Buffer (10 × Ex Taq Buffer, manufactured by Takara Bio Inc.) | 5 μl |
| dNTP (2.5 mM each, manufactured by Takara Bio Inc.) | 4 μl |
| Primer DNA of SEQ ID NO: 4 (100 pmol/μl) | 0.5 μl |
| Primer DNA of SEQ ID NO: 5 (100 pmol/μl) | 0.5 μl |
| *E. coli* in each colony | Subtle quantity |

PCR was performed in a commercial temperature cycler (ROBOCYCLER™; manufactured by Stratagene) using the following conditions: an initial denaturation of 3 min at 94° C., followed by 25 cycles of 60 sec at 94° C., 60 sec at 56° C., 140 sec at 72° C. After the reaction, amplification of the fragments of interest was confirmed by 1% agarose electrophoresis and recombinant plasmid containing the transaminase gene of interest was prepared from the positive colonies. The DNA fragments of interest in the recombinant plasmid were sequenced, and the DNA sequences of the clones were found to have no mutation.

Using the resulting recombinant plasmid, the Rosetta (DE3) strain was transformed. The transformed *E. coli* was spread onto an LB agar plate containing 50 μg/ml ampicillin and 34 μg/ml chloramphenicol, and incubated at 37° C. overnight.

2. Induction of Protein Expression

The recombinant *E. coli* thus obtained was inoculated into 5 ml of LB medium containing 50 μg/ml ampicillin and 34 μg/ml chloramphenicol and incubated at 37° C. overnight.

Next, 50 μl of the pre-culture was added to 5 ml of LB medium containing 50 μg /ml ampicillin and 34 μg/ml chloramphenicol, and the main culture was incubated at 37° C. to an OD660 of 1.0. IPTG was then added to the culture at a final concentration of 1 mM, and the gene expression was induced by incubating it for 1 hour, 3 hours, 5 hours, 7 hours, 9 hours, 20 hours, 30 hours, and 44 hours each at 15° C., 25° C., 37° C., 43° C. that corresponds to 4 degrees below the upper temperature limit for growth, and 46° C. that corresponds to 1 degree below the upper temperature limit for growth. After incubation, bacteria was harvested from 3 ml of the culture, washed with 20 mM potassium phosphate buffer (pH 7.5), and suspended in 20 mM potassium phosphate buffer (pH 7.5) containing 1 mM pyridoxal phosphate. The bacterial suspension was ultrasonicated, followed by centrifugation, and the supernatant was used as cell-free extraction. By heat-treating this cell-free extraction at 80° C. for 30 min, *E. coli*-derived aminotransferase was inactivated, insoluble debris was removed by centrifugation, and the supernatant was used as a crude enzyme.

3. Method for Confirming Enzyme Activity

200 μl of reaction mixture containing 30 mM L-phenylalanine, 60 mM 2-oxoglutaric acid, 0.5 mM pyridoxal phosphate, 100 mM potassium phosphate buffer (pH 7.5), and 50 μl of the above-mentioned crude enzyme was incubated at 80° C. for 30 min, and then the reaction was stopped by adding 50 μl of a 30% trichloroacetic acid aqueous solution. The glutamic acid generated in the reaction was derivatized with the Marfey's reagent and quantified by HPLC.

The result of measurement of the enzyme activity is shown in FIG. 1.

4. Electrophoresis

Figure 2:
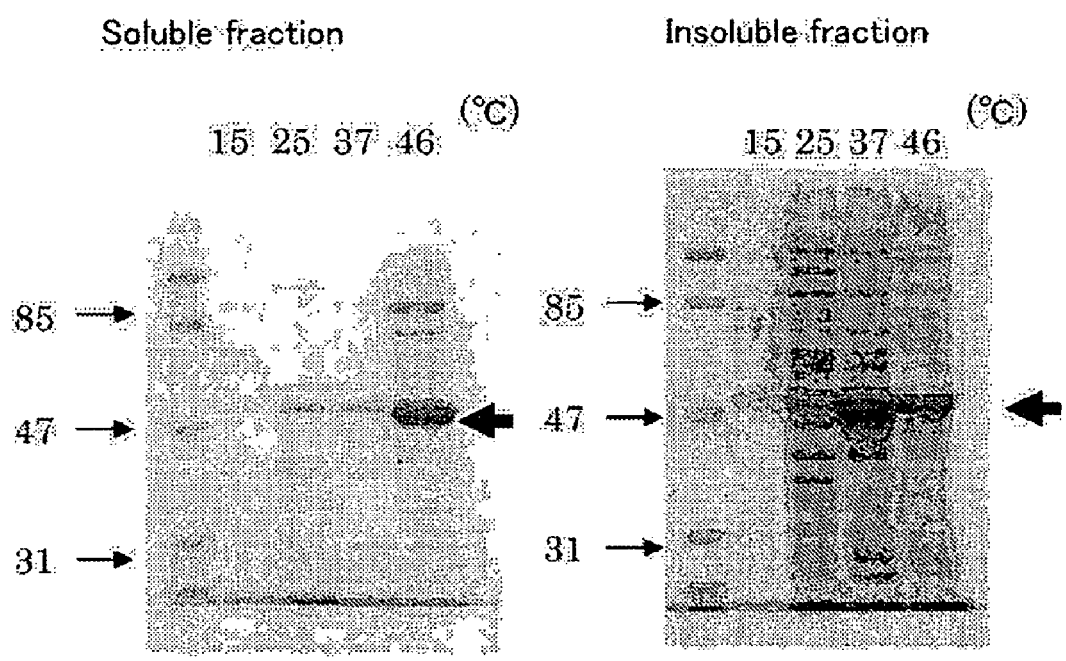
FIG. 2 shows a result of electrophoresis in Example 1 performed according to the present invention. The arrowhead on the right side of the gel indicates the protein expressed.

The samples of the crude enzyme solution obtained from bacteria which were cultured for the induction for 20 hours at temperatures of 15° C., 25° C., 37° C., and 46° C., were mixed with an equivalent volume of 2× sample buffer composed of 0.1 M tris-hydrochloric acid (pH 6.8), 4% SDS, 12% β-mercaptoethanol, 20% glycerol, and a subtle quantity of bromophenol blue. The soluble proteins contained in the samples were analyzed by SDS-polyacrylamide gel electrophoresis. In addition, the precipitates resulting from ultrasonication were suspended in a 1× sample buffer and insoluble proteins were analyzed by SDS-polyacrylamide gel electrophoresis. The result of the electrophoresis is shown in FIG. 2.

EXAMPLE 2

Recombinant *E. coli* was obtained, the protein expression was induced, and the crude enzyme solutions were obtained according to Example 1, except that the transaminase gene (PH1423) of the hyperthermophile *Pyrococcus horikosii* was used as a foreign gene. The nucleotide sequence of PH1423 used here is shown in SEQ ID NO: 6 and the primers for the PCR reaction are shown in SEQ ID NOs: 7 and 8. *Pyrococcus horikoshii* OT3 is a hyperthermophile isolated from a hydrothermal fluid in Okinawa Prefecture by the manned deep-sea investigation vessel "Shinkai 2000" in the DeepStar project. Its genome information has been published by the National Institute of Technology and Evaluation.

Figure 3:
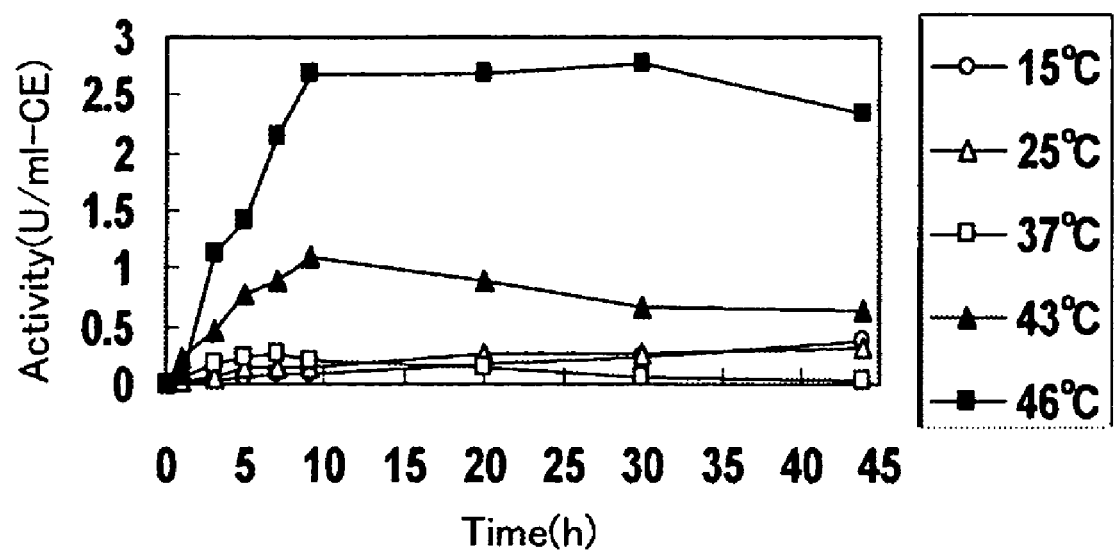
FIG. 3 shows a result of a measurement of enzyme activity in Example 2 performed according to the present invention.

20 μl of reaction mixture containing 40 mM L-ornithine, 60 mM 2-oxoglutaric acid, 0.5 mM pyridoxal phosphate, 100 mM potassium phosphate buffer (pH 7.5), and 10 μl of the above-mentioned crude enzyme was incubated at 80° C. for 10 min, and then the reaction was stopped by adding 50 μl of a 30% trichloroacetic acid aqueous solution. The result of measurement of the enzyme activity is shown in FIG. 3.

Figure 4:
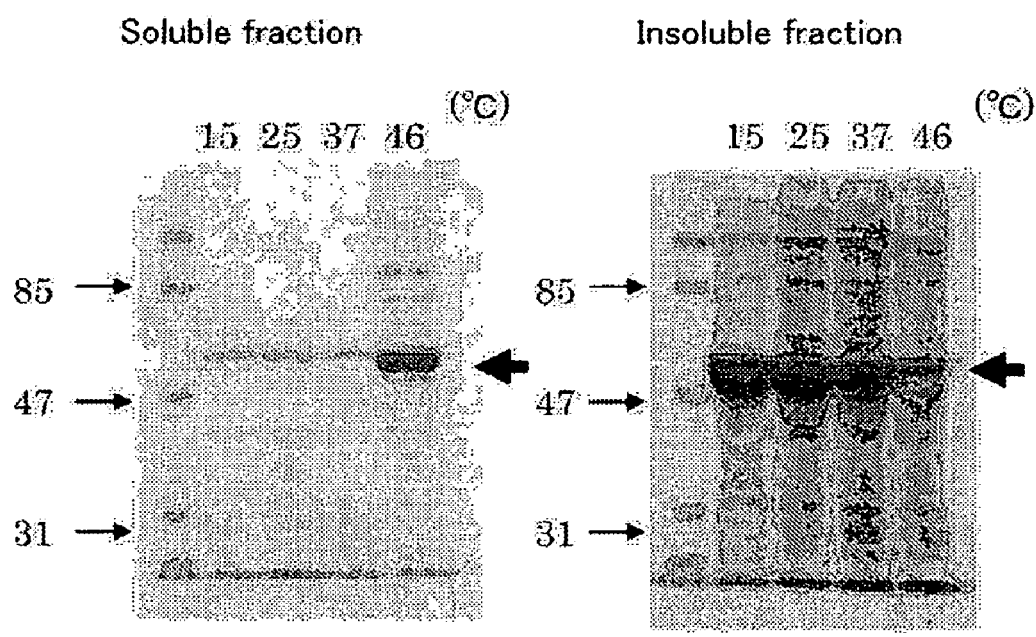
FIG. 4 shows a result of electrophoresis in Example 2 performed according to the present invention. The arrowhead on the right side of the gel indicates the protein expressed.

In addition, the soluble proteins and non-soluble proteins were analyzed by SDS-polyacrylamide gel electrophoresis in the same procedure as in Example 1. The result of electrophoresis is shown in FIG. 4.

EXAMPLE 3

Recombinant *E. coli* was obtained, protein expression was induced, and crude enzyme solutions were obtained according to Example 1, except that the transaminase gene (APE0457) of the hyperthermophile *Aeropyrum perni* was used as a foreign gene. The nucleotide sequence of the transaminase gene (APE0457) used here is shown in SEQ ID NO: 9 and the primers for the PCR reaction are shown in SEQ ID NOs: 10 and 11.

Figure 5:
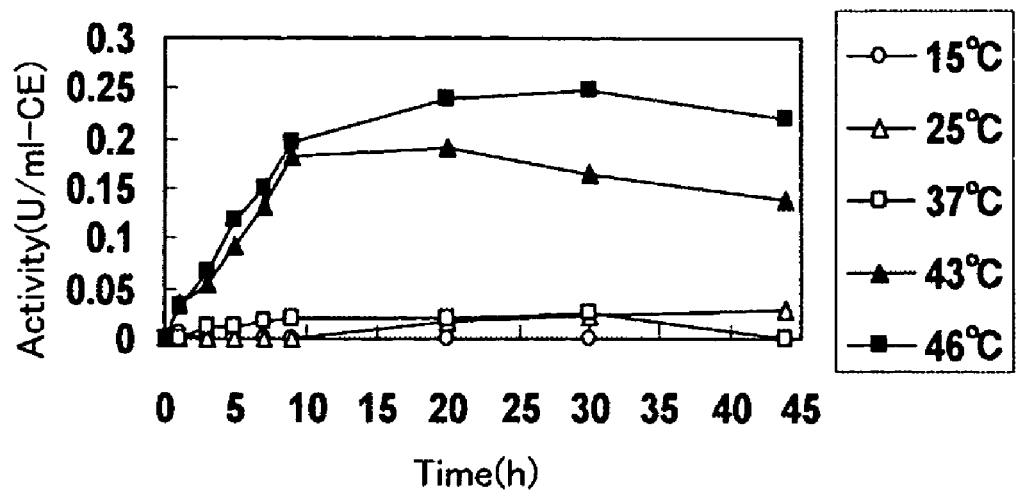
FIG. 5 shows a result of a measurement of enzyme activity in Example 3 performed according to the present invention

Enzyme activities were measured in the same procedure as an Example 2. The result of measurement of the enzyme activities is shown in FIG. 5.

Figure 6:
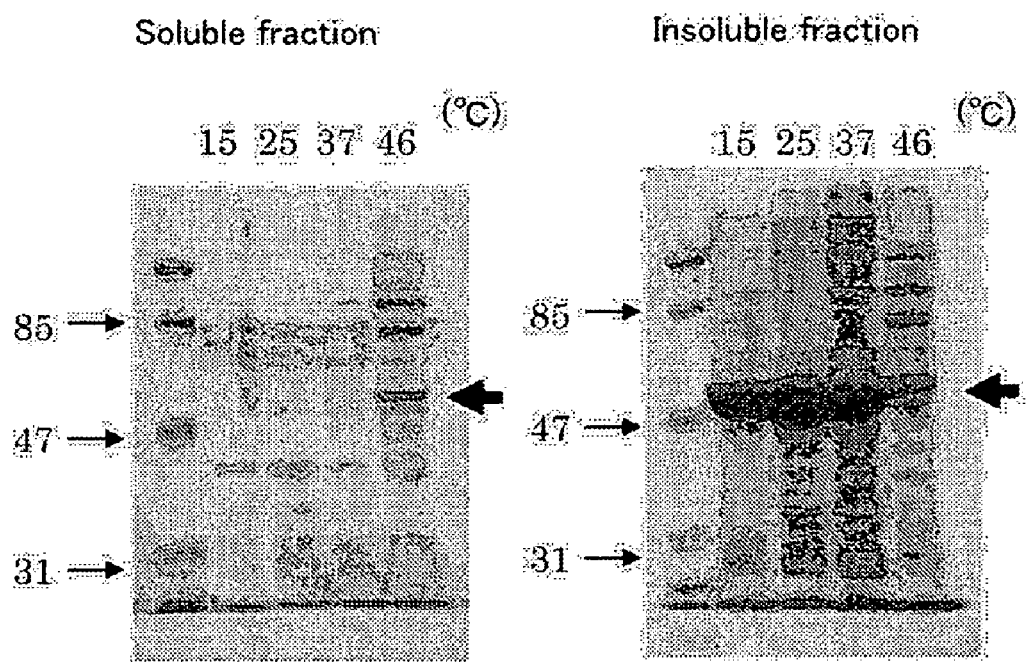
FIG. 6 shows a result of electrophoresis in Example 3 performed according to the present invention. The arrowhead on the right side of the gel indicates the protein expressed.

In addition, the soluble proteins and non-soluble proteins were analyzed by SDS-polyacrylamide gel electrophoresis in the same procedure as in Example 1. The result of electrophoresis is shown in FIG. 6.

EXAMPLE 4

Recombinant *E. coli* was obtained, protein expression was induced, and crude enzyme solutions were obtained according to Example 1, except that the transaminase gene (ST1225) of the hyperthermophile *Sulfolobus tokodaii* was used as a foreign gene. The nucleotide sequence of the transaminase gene (ST1225) used here is shown in SEQ ID NO: 12 and the primers for the PCR reaction are shown in SEQ ID NOs: 13 and 14. *Sulfolobus tokodaii* is an aerobic and acidophilic thermophile isolated from one of the hot springs in Beppu-Onsen of Oita Prefecture, which is capable of decomposing hydrogen sulfide by itself. Its genome information has been published by the National Institute of Technology and Evaluation.

Figure 7:
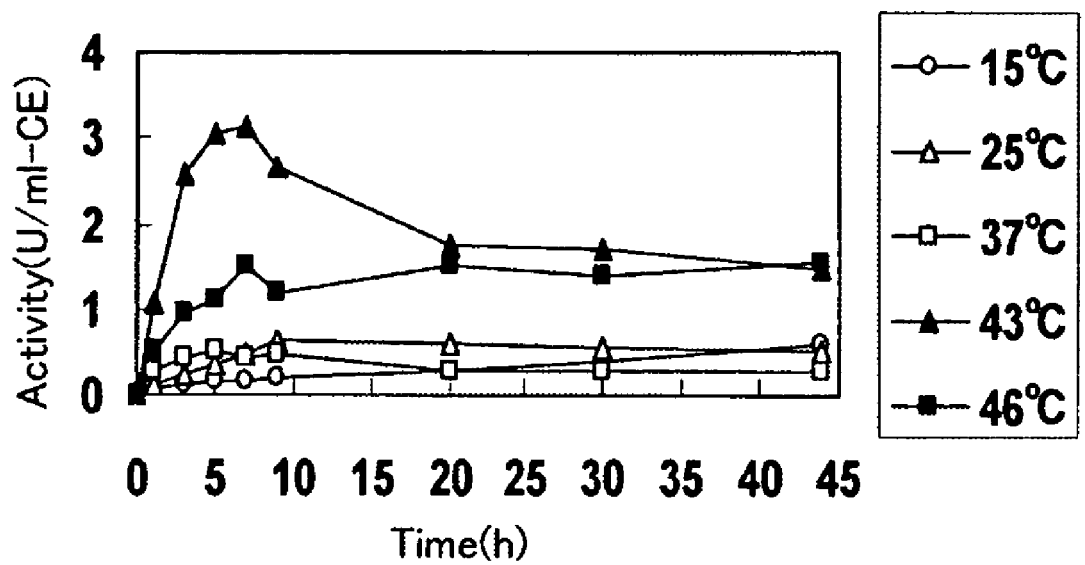
FIG. 7 shows a result of a measurement of enzyme activity in Example 4 performed according to the present invention.

Enzyme activities were measured in the same procedure as an Example 1. The result of measurement of enzyme activity is shown in FIG. 7.

Figure 8:
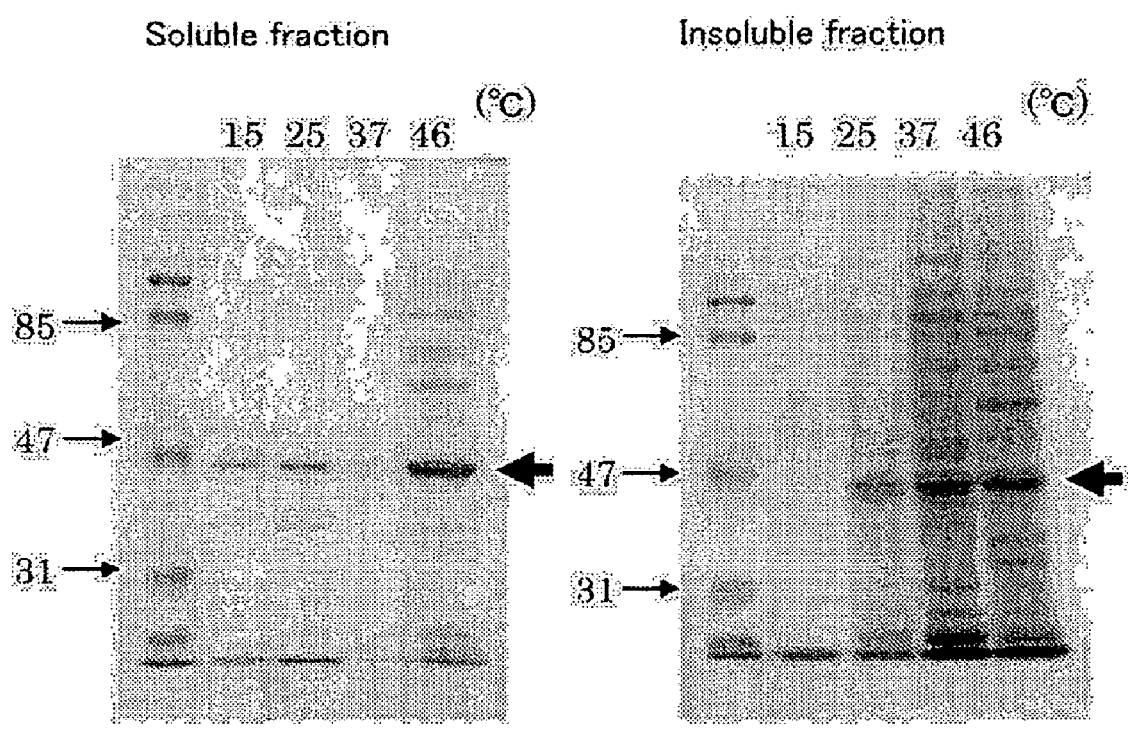
FIG. 8 shows a result of electrophoresis in Example 4 performed according to the present invention. The arrowhead on the right side of the gel indicates the protein expressed.

In addition, the soluble proteins and non-soluble proteins were analyzed by SDS-polyacrylamide gel electrophoresis in the same procedure as in Example 1. The result of electrophoresis is shown in FIG. 8.

RESULTS AND DISCUSSION

FIGS. 1, 3, 5, and 7 indicate that the enzyme activities markedly increased when the method according to the present invention was used, compared with the results obtained when the culture temperature for the induction was 15° C., 25° C., or 37° C.

In all the Examples, it was found that the enzyme activity increased 5 to 10-fold when the culture temperature for the induction was 46° C., compared with the results of the control experiments obtained when the culture temperature for the induction was 15° C., 25° C., or 37° C. Further, FIG. 7 indicates that, depending on the protein to be expressed, enzyme activity increased 3 to 4-fold when the culture temperature for the induction is 43° C., compared with the results obtained at 15° C., 25° C., or 37° C.

Moreover, in all the Examples, it could be confirmed that only a small amount of both soluble and insoluble proteins was obtained when the protein expression was induced at 15° C. or 25° C.; that only a small amount of soluble proteins but a large amount of insoluble proteins were obtained when the protein expression was induced at 37° C.; and that signals for soluble proteins were clearly visible, whereas signals for insoluble proteins were relatively faint, when the protein expression was induced at 46° C.

In conclusion, it was shown that by using the method herein, a protein of interest can be solubilized with its activity maintained.

What is claimed is:

1. A method for producing a transaminase protein encoded by a transaminase gene comprising culturing *E. coli*, into which the transaminase gene has been introduced, in the temperature range equal to or higher than 44° C. and lower than 47° C. after introduction of expression of the transaminase gene, wherein the transaminase gene is selected from the group consisting of the transaminase gene APE2248 as set forth in SEQ ID NO:1 of hyperthermophile *Aeropyrum pernix*, the transaminase gene PH1423 as set forth in SEQ ID NO:6 of hyperthermophile *Pyrococcus horikoshii*, the transaminase gene APE0457 as set forth in SEQ ID NO: 9 of hyperthermophile *Aeropyrum pernix*, and the transaminase gene ST1225 as set forth in SEQ ID NO:12 of hyperthermophile *Sulfolobus tokodait*.

2. The method of claim 1, wherein the transaminase gene is the transaminase gene APE2248 as set forth in SEQ ID NO:1 of hyperthermophile *Aeropyrum pernix*.

3. The method of claim 1, wherein the transaminase gene is the transaminase gene PH1423 as set forth in SEQ ID NO:6 of hyperthermophile *Pyrococcus horikoshii*.

4. The method of claim 1, wherein the transaminase gene is the transaminase gene APE0457 as set forth in SEQ ID NO:9 of hyperthermophile *Aeropyrum pernix*.

5. The method of claim 1, wherein the transaminase gene is the transaminase gene ST1225 as set forth in SEQ ID NO:12 of hyperthermophile *Sulfolobus tokodaii*.

* * * * *